(12) United States Patent
Goto et al.

(10) Patent No.: US 7,838,269 B2
(45) Date of Patent: Nov. 23, 2010

(54) GENE DETECTING METHOD

(75) Inventors: Masahiro Goto, Fukuoka (JP);
Hirofumi Ichinose, Fukuoka (JP);
Momoko Kitaoka, Fukuoka (JP);
Nobuko Okamura, Fukuoka (JP)

(73) Assignee: Japan Science and Technology Agency, Saitama (JP)

( * ) Notice: Subject to any disclaimer, the term of this patent is extended or adjusted under 35 U.S.C. 154(b) by 299 days.

(21) Appl. No.: 11/884,814

(22) PCT Filed: Feb. 17, 2006

(86) PCT No.: PCT/JP2006/302824

§ 371 (c)(1),
(2), (4) Date: Aug. 20, 2007

(87) PCT Pub. No.: WO2006/088126

PCT Pub. Date: Aug. 24, 2006

(65) Prior Publication Data

US 2008/0274464 A1 Nov. 6, 2008

(30) Foreign Application Priority Data

Feb. 18, 2005 (JP) ............................. 2005-041479

(51) Int. Cl.
*C12P 19/34* (2006.01)
*C07H 21/04* (2006.01)

(52) U.S. Cl. ..................... 435/91.2; 536/24.3

(58) Field of Classification Search ................. None
See application file for complete search history.

(56) References Cited

U.S. PATENT DOCUMENTS 5,256,555 A 10/1993 Milburn et al.

| | | | |
|---|---|---|---|
| 6,063,572 A * | 5/2000 | Ishiguro et al. | 435/6 |
| 2002/0037507 A1* | 3/2002 | WalkerPeach et al. | 435/6 |
| 2002/0106653 A1 | 8/2002 | Kurane et al. | |
| 2008/0274464 A1 | 11/2008 | Goto et al. | |

FOREIGN PATENT DOCUMENTS

EP 1295941 A1 * 3/2003

OTHER PUBLICATIONS

Bernard et al. Color multiplexing hybridization probes using the apolipoprotein E locus as a model system for genotyping. Analytical Biochemistry 273:221-228 (1999).*

(Continued)

*Primary Examiner*—Samuel Woolwine
(74) *Attorney, Agent, or Firm*—Fay Sharpe LLP (57) ABSTRACT

Disclosed is a gene detecting method for determining mutation of a specific base or presence/absence of a specific base in a target gene. There are provided a the target gene sample and a control gene sample having a base sequence which is wild-type or standard-type with respect to the target gene. The method comprises steps of (i) independently subjecting the target gene sample and the control gene sample to a PCR reaction for amplification, using primers having an RNA polymerase promoter sequence at the 5'-end thereof, (ii) independently subjecting the double-stranded DNAs produced by said PCR reaction from the target gene sample and from the control gene sample, to an in vitro transcription reaction to form a single-stranded RNA, (iii) independently hybridizing the single-stranded RNAs with a fluorescence-labeled probe composed of a single-stranded DNA having a base sequence complementary to at least part of the base sequence of the control gene and being combined with a fluorescent dye, to form an RNA/DNA hybrid, and then (iv) comparing the fluorescence intensity of the RNA/DNA hybrid derived from the target gene sample with that of the RNA/DNA hybrid derived from the control gene sample.

2 Claims, 7 Drawing Sheets

OTHER PUBLICATIONS

Ichinose et al. Detection of single-base mutations by fluorogenic ribonuclease protection assay. Analytical Chemistry 77:7047-53 (2005).*

Yamane. MagiProbe: a novel fluorescence quenching-based oligonucleotide probe carrying a fluorophore and an intercalator. Nucleic Acids Research 30(19): e97, pp. 1-8 (2002).*

Carlson, et al., Identification and characterization of phosphoseryl-tRNA[Ser] Sec kinase, *PNAS*, vol. 101, No. 35, 2004, pp. 12848-12853, XP003005892.

D'Avino et al., Mutations in sticky lead to defective organization of the contractile ring during cytokinesis and are enhanced by Rho and suppressed by Rac, *J. Cell Biol.*, vol. 166, 2004, pp. 61-71, XP003005891.

Khyrul Islam, et al., Pyrophosphatase of the Roundworm Ascaris suum Plays an Essential Role in the Worm's Molting and Development, *Infect. Immun.*, vol. 73, No. 4, Apr. 2005, pp. 1995-2004, XP003005889.

Livache, et al., Detection of HIV1 DNA in Biological Samples by an Homogeneous Assay: Fluoroescence Measurement of Double-Stranded RNA Synthesized from Amplified DNA, *Anal Biochem.*, vol. 217, No. 2, pp. 248-254 (1994).

Promega, T7 RiboMAX™ Express Large Scale RNA Production System, Instructions for Use of Product P1320, *Technical Bulletin*, Aug. 2005, pp. 1-9, XP003005888.

* cited by examiner

Fig.1

D.S. (Double-stranded)
S.S. (Single-stranded)
F.L. (Fluorescence-labeled)
C.C. (Completely complementary)
I.C. (Incompletely complementary)
F.I. (Fluorescence intensity)

Fig. 2

(A) Base sequence of wild type HBV gene, Lamivudine-effective

5'-CC CAC TGT TTG GCT TTC AGT TAT

| I. | Pacific northern bluefin (*Thunnus thynnus orientalis*) |
| II. | Atlantic northern bluefin (*Thunnus thynnus thynnus*) |
| III. | Southern bluefin (*Thunnus maccoyii*) |
| IV. | Bigeye (*Thunnus obesus*) |
| V. | Yellowfin (*Thunnus albacares*) |
| VI. | Albacore (*Thunnus alalunga*) |

GENE DETECTING METHOD

TECHNICAL FIELD

The present invention relates to a method of detecting a gene, by which mutation or presence/absence of a specific base in the gene can be detected for a variety of purposes.

BACKGROUND ART

Upon the completion of the Human Genome Project, the entire base sequence of the human genome became known and numerous genes are being disclosed along with their functions. Detection of individual gene mutation or abnormality has therefore become increasingly important as it will contribute to the development of so-called post-genome medicine, therapy, diagnosis and the like. For example, it is expected that the detection of a single nucleotide polymorphism (SNP) in humans will provide basic information for tailor-made medical services or personalized medicine adapted individual differences.

Recently, the need has also intensified for DNA analysis aimed at inhibiting and preventing false representation of food products so that there can be secured agricultural products, marine products, livestock products and the like which are safe and meet consumer demand.

Gene detection is also useful as a measure to determine if a microorganism present in the ground, water or atmosphere is harmful or detoxicated, due to natural or unnatural environmental variation: It is important to know the alteration of the microorganism, for example, whether or not the microorganism has a specific base which is involved in making it harmful.

Techniques primarily employed hitherto for gene detection for the above-mentioned purposes include amplification of a target gene by RCR reaction, followed by analysis of the gene by direct sequencing or capillary electrophoresis to determine the presence of mutation. A real-time PCR reaction method is also known in which a DNA probe is used to monitor the RCR reaction so that a target gene is quantified for the analysis of polymorphism or mutation [For example, Japanese Patent Application Publication No.2002-275 (Patent Reference 1), Japanese Patent Application Publication No.2002-119291 (Patent Reference 2)].

However, these conventional methods have a drawback that only a limited amount of DNA is obtained by the RCR reaction and, a high level of knowledge and skill are needed for obtaining reproducible and reliable results. Shortcomings are also found in that there are needed costly analytical devices such as a DNA sequencer and that a long time is required for analysis. If electrophoresis is employed, more time and effort will be needed for analysis.

Patent Reference 1: Japanese Patent Application No.2002-275

Patent Reference 2: Japanese Patent Application No.2002-119291

DISCLOSURE OF THE INVENTION

The Problems to be Solved by the Invention

The object of the present invention is to provide a novel gene detecting method which enables a highly accurate analysis with a small amount of sample and a simple and easy determination of mutation of a specific base or presence/absence of a specific base in the gene.

The Means to Solve the Problems

The present inventors found, through extensive studies, that the above mentioned object can be achieved by transcribing a target gene into RNA followed by hybridization of the RNA with a fluorescence-labeled probe and, preferably, treating the thus obtained hybrid with ribonuclease.

Thus, the present invention provide a gene detecting method for determining mutation of a specific base or presence/absence of a specific base in a target gene, wherein there are provided a target gene sample and a control gene sample having a base sequence which is wild-type or standard-type with respect to the target gene, which method comprises steps of (i) independently subjecting the target gene sample and the control gene sample to a PCR reaction for amplification, using primers having an RNA polymerase promoter sequence at the 5'-end thereof, (ii) independently subjecting the double-stranded DNAs produced by said PCR reaction from the target gene sample and from the control gene sample, to an in vitro transcription reaction to form a single-stranded RNA, (iii) independently hybridizing the single-stranded RNAs with a fluorescence-labeled probe composed of a single-stranded DNA having a base sequence complementary to at least part of the base sequence of the control gene and being combined with a fluorescent dye, to form an RNA/DNA hybrid, and then (iv) comparing the fluorescence intensity of the RNA/DNA hybrid derived from the target gene sample with that of the RNA/DNA hybrid derived from the control gene sample.

According to a preferred embodiment of the present invention, in the step of (iii) of forming RNA/DNA hybrids, each single-stranded RNA is hybridized with a fluorescence-quenching probe composed of a single-stranded DNA having a base sequence complementary to at least part of the base sequence of the control gene and being combined with a quenching dye which serves to quench the fluorescence dye.

According to further preferred embodiment of the present invention, each RNA/DNA hybrid obtained by the step (iii) is subjected to an RNA decomposition reaction using RNase, followed by the step (iv) of comparing the fluorescence intensities.

ADVANTAGEOUS EFFECTS OF THE INVENTION

By subjecting the PCR products to the in vitro transcription reactions in accordance with the present invention, the gene samples can be prepared in the form of single-stranded RNA in concentrations more than 100 times the amount of sample in the conventional method. Thus, it is possible to overcome the issue of low reliability experienced by the conventional method owing to the limited amount of sample obtained solely by a PCR reaction. The method of the present invention is carried out without the operation of electrophoresis, and thus the time required for analysis is greatly shortened. The sequence of the operations of the method of the present invention can be implemented in an easy and rapid manner without special knowledge and expert skill. Since no special equipment is needed for analysis, the analytical method of the present invention can be adapted for use in a variety of research establishments.

BEST MODE FOR CARRYING OUT THE INVENTION

Figure 1:
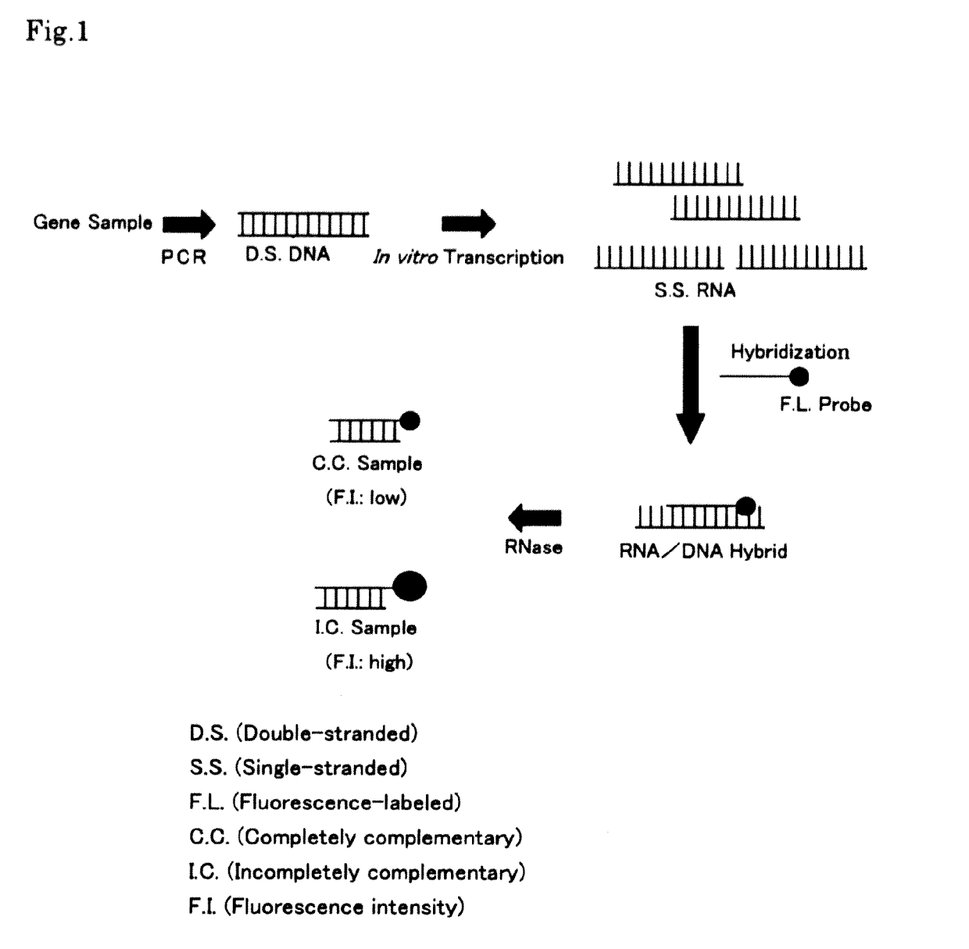
FIG. 1 schematically illustrates the respective steps of the gene detecting method of the present invention.

The mode for carrying out the present invention will be detailed in the following with reference to the respective steps of the present invention as illustrated in FIG. 1.

PCR Reaction

As a first step of the gene detecting method in accordance with the present invention, a target gene sample (sample of the gene to be examined) and a control gene sample (sample of a gene having a wild-type or standard-type base sequence with respect to the target gene) are subjected to PCR (polymerase chain reaction), wherein the present invention features a subsequent step of synthesizing a large amount of single-stranded RNA from the PCR products as template, thereby achieving a quantum increase in sample amount. Thus, primers for use in the amplification of the respective gene samples by PCR in the present invention include not only a base sequence specific to the genes as in a usual PCR reaction, but also a RNA polymerase promoter sequence at the 5'-end thereof.

The PCR reaction in the present invention is not a special one, except that there are used primers having RNA polymerase promoter sequence. Thus, the target gene sample and the control gene sample, whose genes are composed of double-stranded DNA, are each mixed with dNTP and thermal resistant DNA polymerase in addition to the above-mentioned primers. Then, as well known, a cycle of the thermal denaturation of double-stranded DNA, the annealing of primers, and the elongation reaction by polymerase is repeated (generally, 30-40 cycles).

RNA polymerase promoter sequence to be linked to the 5'-end of the primers for use in the step of PCR in the gene detecting method of the present invention is a promoter sequence of DNA-dependent RNA polymerase (transcriptase). A preferred but nonlimiting example of RNA polymerase promoter sequence is T7 RNA polymerase recognition sequence [5'-TAATACGACTCACTATAGGG (SEQ ID NO:1)-3']. Besides this, SP3 RNA polymerase and the like can be used.

Any thermal resistant DNA polymerase generally used in the art can be used in the step of PCR reaction in the method of the present invention. Examples include, but not limited to, a thermal resistant DNA polymerase under the trade name, Pyrobest, commercially available from Takara.

In Vitro Transcriptase Reaction

According to the present invention, each of the double-stranded DNAs obtained from the PCR reactions as mentioned above is subjected to an in vitro transcription reaction. As the double-stranded DNA, the PCR product, has an RNA polymerase promoter sequence, it undergoes the transcription reaction through the action of RNA polymerase so as to produce single-stranded RNA in which the PCR product serves as template.

The in vitro transcription reaction may be carried using any commercially available in vitro transcription reaction kit. Examples of in vitro transcription reaction kits include, but are not limited to, "T7 Ribo MAX™ Express Large Scale RNA Production System" (Promega).

There is obtained only a small amount of DNA only by a PCR reaction because of limited amplification of DNA. By contrast, the present invention enables a drastic increase in the amount of the samples (the target gene sample and the control gene sample), as single-stranded RNA by subjecting the PCR products to in vitro transcription reaction-generally more than 100 times in concentration.

Hybridization

In the gene detecting method of the present invention, the single-stranded RNA obtained by the in vitro transcription reaction as mentioned above is then hybridized with a fluorescence-labeled probe to form RNA/DNA hybrid (duplex). The fluorescence-labeled probe is composed of a single-stranded DNA having a sequence complementary to at least part of the base sequence of the control gene and being combined with a fluorescence dye. The fluorescence dye covalently combines to the base at the end (5'-end or 3'-end) of the probe, wherein the fluorescence-labeled probe is preferably designed in such manner that a base to be detected is positioned as near as possible to the base with which the fluorescence dye combines, i.e. at the end of the probe or at a position of within three bases from the terminal base.

Figure 2:
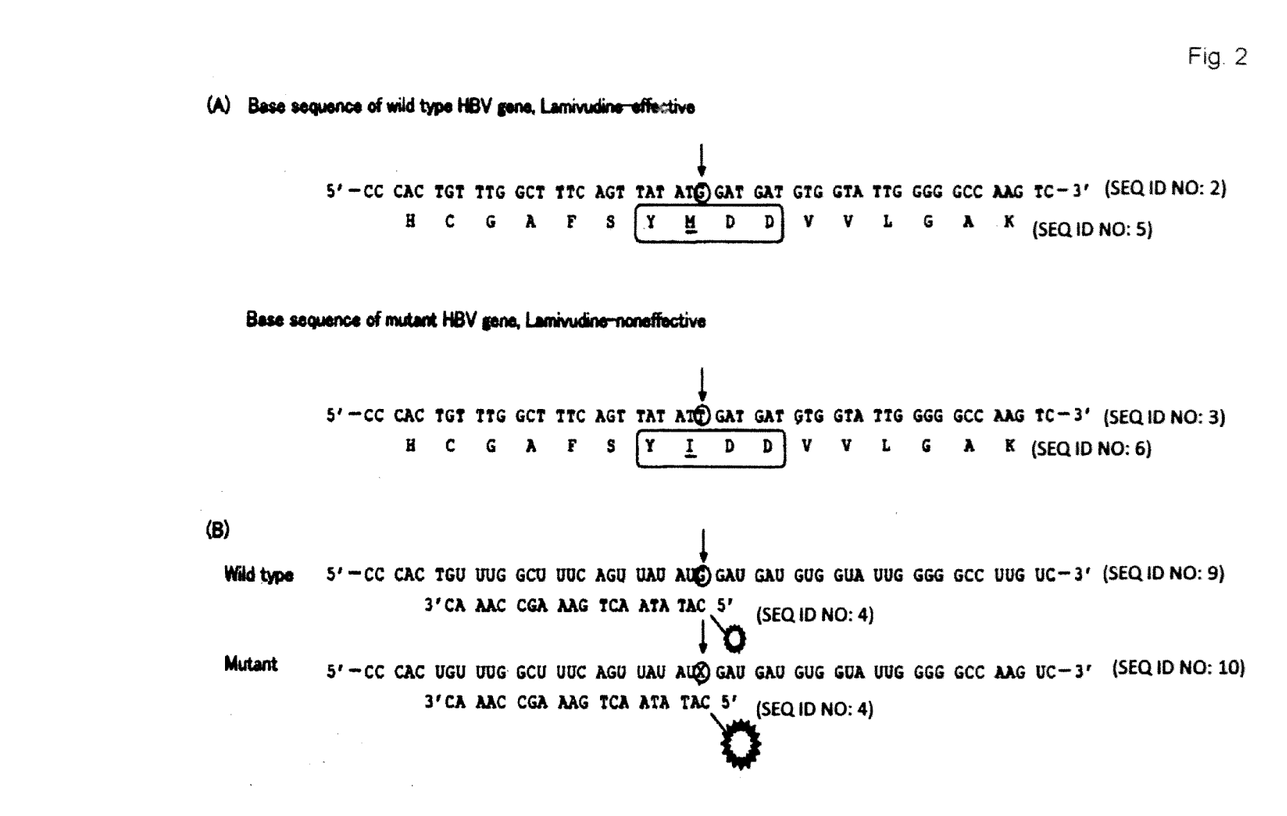
FIG. 2 shows gene arrangements of HBV (A), and RNA/DNA hybrids derived therefrom, as an example to which the present invention is applied (Example 1).

FIG. 2 illustrates an example of the relationship between base sequence of a target gene and fluorescence-labeled probe therefor. FIG. 2 (A) shows the base sequence of wild-type human hepatitis B virus (HBV) gene (SEQ ID NO:2), against which Lamivudine therapy is effective, and the base sequence of mutant human HBV gene (SEQ ID NO:3), against which Lamivudine therapy is not effective, wherein Lamivudine therapy is expected to be a tailor made or personalized medical treatment based on single nucleotide polymorphism. It is considered that the mutation of amino acid M(lysine) in the wild-type into I(isoleucin) resulting from the mutation of base G in the wild-type into T produces the Lamivudine resistance. In FIG. 2 (B) there is illustrated a fluorescence-labeled probe designed to detect such single nucleotide polymorphism in accordance with the present invention. The probe (5'-CAT ATA ACT GAA AGC CAA AC-3') (SEQ ID NO:4) is labeled with a fluorescence dye which is combined to the base at the 5'-end. In the example as illustrated in the figure, a base to be detected in the target gene (in the form of single-stranded RNA) is present in the position corresponding to the terminal base of the probe.

Thus, the gene mutation can be detected by comparing the fluorescence intensity of RNA/DNA hybrid derived from the target gene sample to be tested (the lower, FIG. 2 (B)) with that of RNA/DNA hybrid derived from the control gene sample (the upper, FIG. 2 (B)). In the example illustrated in FIG. 2, the RNA/DNA hybrid derived from the wild-type (control gene), in which the base to be detected is G, exhibits the degree of fluorescence quenching higher than the RNA/DNA hybrid derived from the mutant gene in which the mutation occurs at the corresponding position (designated by X) (cf. Examples).

As the fluorescence dye which is covalently combined with single-stranded DNA for use in the present invention, a variety of conventionally known fluorescence dyes can be used. Examples of preferred fluoresce dye include, but are not limited to, FITC (fluorescein-isothiocyanate), TAMRA (5-carboxy-tetramethyl-rhodamine), FAM(5-carboxy-fluorescein), HEX(6-carboxy-2,4,4',5',7,7'-hexachloro fluorescein), Rhodamine, Cy3[indodicarbocyanine-3-1-o-(2-cyano-ethyl)-N,N'-diisopropane)].

According to a preferred embodiment of the present invention, each single-stranded RNA obtained by the above-mentioned transcription reaction is hybridized not only with a fluorescence-labeled probe but also with a fluorescence-quenching probe. The fluorescence-quenching probe is composed of a single-stranded DNA having a base sequence complementary to at least part of the base sequence of the control gene and being combined with a quenching dye serving to quench the fluorescence dye. Thus, the fluorescence-quenching dye is composed of a molecule which has an absorption band overlapping with the fluorescence-emitting region of the fluorescence dye.

Generally, a fluorescence dye and fluorescence-quenching dye are combined to the end of a fluorescence-labeled probe and the end of a fluorescence-quenching probe, respectively. When the fluorescence dye is combined to the 5'-end of the fluorescence-labeled probe, the fluorescence-quenching dye is combined to the 3'-end of the fluorescence-quenching probe. In all cases, the base to be detected should positioned as near as possible to the bases with which the fluorescence dye and the fluorescence-quenching dye are combined, more specifically, at a position of corresponding to the terminal base or within three bases from the terminal base (cf. FIGS. 6 and 9).

Examples of preferred, applicable combinations of fluorescence dye with fluorescence-quenching dye include, but are not limited to, fluorescence dye FITC with fluorescence quenching dye BHQ-1[4'-(2-nitro)-4-toluylidazol-2'-methoxy-5'-methoxy-azobenzene-4''-(N-ethyl)-N-ethyl-2-cyano-ethyl-(N,N-diisopropane))]. Other examples include fluorescence dye Rhodamine, TAMARA or Cy3 with fluorescence quenching dye BHQ-2'[4'-(4'-nitro-phenyldiazo)-2'-methoxy-5'-methoxy-azobenzene-4''-(N-ethyl-2-O-(4,4'-dimethoxytrityl))-N-ethyl-2-O-glycolate].

Thus, according to the fluormetry in which there is used RNA hybridized with a fluorescence-labeled probe and a fluorescence-quenching probe, a greatly enhanced rate of fluorescence quenching is attained, thereby enabling a highly accurate detection of the mutation or the presence/absence of a specific base in a target gene.

As mentioned previously, a fluorescence-labeled probe of a single-stranded DNA combined with a fluorescence dye has been heretofore used as a primer to monitor the PCR reaction in the real-time PCR method (Patent Reference Nos. 1 and 2). However, there are no examples in which single-stranded RNAs, from gene samples, are hybridized with a fluorescence-labeled probe, and preferably, further with a fluorescence-quenching probe and subjected to comparison in fluorescence intensity for gene detection.

The gene detecting method of the present invention is suitable for use in the detection of the gene mutation at a single base level, i.e., SNP (single nucleotide polymorphism). While FIGS. 1 and 2 illustrate an example in which one SNP is present, the method of the present invention can also be applied to a target gene in which a plurality of SNPs are present. In the latter case, the bases to be detected are separated from each other preferably by a distance of at least about thirty bases, in which fluorescence dyes, preferably different types of fluorescence dyes, are combined to the respective bases to be detected at a position as near as possible. Furthermore, the present invention can be applied to plural target genes, each having a SNP, so as to detect such mutations simultaneously.

According to the present invention, gene mutation can be detected by comparing the fluorescence intensity of RNA/DNA hybrid derived from a target gene sample with that of RNA/DNA hybrid derived from the control gene sample, as described. Herein, in a particularly preferred embodiment of the present invention, the RNA/DNA hybrids are subjected to RNA decomposition reaction using an RNase (ribonuclease), followed by such comparison in the fluorescence intensity. This decomposes and removes part of the RNA which has not hybridized with the fluorescence-labeled probe, so as to produce more pronounced difference in the fluorescence intensity (the fluorescence quenching rate), thereby enabling easy and more accurate detection of the mutation by such comparison. Furthermore, as described previously, concurrently with a fluorescence-labeled probe is used a fluorescence-quenching probe combined with a molecule with an absorption band overlapping with the fluorescence-emitting region of the fluorescence dye being positioned in the vicinity of the dye, so as to attain a markedly large (fluorescence) quenching rate for highly accurate detection of the mutation.

The present invention will now be explained in the following more specifically with reference to Examples, but the present invention is not limited in any way by such Examples.

EXAMPLE 1

Detection of Gene Mutation Observed in Hepatitis B Virus 1.1 Preparation of DNA (PCR)

PCR reactions were carried out using plasmid gene containing hepatitis B virus gene (wild-type or control gene) (FIG. 2A, SEQ ID NO:2) and plasmid gene containing mutant hepatitis B virus gene (target gene) (FIG. 2A, SEQ ID NO:3) (cf. FIG. 1 (A)) as template, to obtain gene fragments containing the sites to be analyzed (to be detected), wherein each plasmid gene was composed of pUC18 (FIG. 2A, SEQ ID NO:5 and SEQ ID NO:6) with the SmaI site thereof being linked with hepatitis B virus gene. As PCR primers there were used primer 1 having T7 RNA polymerase promoter sequence at the 5'-end thereof (SEQ ID NO: 7), and primer 2 which is gene specific (SEQ ID NO:8) for DNA polymerase, Pyrobest® (TaKaRa). The reaction conditions are as follows:

Composition for PCR (100 μl): template DNA (<1 μg), DNA polymerase Pyrobest® (2.5 unit), primer 1 (1 μm), primer 2 (1 μm), dNTP (200 μm), 1×Pyrobest Buffer II.

PCR conditions: One cycle of thermal denaturation at 95° C., 15 sec, followed by thirty-five cycles of thermal denaturation at 95° C., 15 sec, annealing at 55° C., 30 sec, and then elongation reaction at 72° C., 30 sec.

Primer 1: 5'-ATGATCACTAATACGACTCACTATAGGGCTTTCCCCC ACTGTTTGGC-3' (SEQ ID NO: 7)

Primer 2: 5'-GGTACCCCAACTTCCAATTACATAT-3' (SEQ ID NO: 8)

1.2 Preparation of RNA Samples (In vitro Transcription)

The PCR products obtained by the step of 1.1 were subjected to in vitro transcription reactions to prepare single-stranded RNA pUC18 (FIG. 2B, SEQ ID NO:9 and SEQ ID NO:10). The transcription reactions were carried out using T7 RiboMAX™ Express Large Scale RNA Production System (Promega). The RNA products are recovered through ethanol precipitation, followed by redissolution in sterilized water to prepare RNA samples. The reaction conditions were as follows:

Composition for the reaction (20 µL): PCR product (2 µL). Enzyme Mix, T7 Express (2 µl), 1×RiboMAX™ Express T7 buffer.

Reaction conditions: Following the synthesis reaction (at 30° C., 30 min.), each RNA sample was recovered using Dr. GenTLM™ Precipitation Carrier (TaKaRa).

1.3.1 Hybridization and RNA Decomposition

Each fluorescence-labeled probe used was composed of oligoDNA (5'-CATATAACTGAAAGCCAAAC-3') (SEQ ID NO:11) being combined with one of various fluorescence dyes as shown in FIG. 2 (B).

Each fluorescence-labeled probe (40 pmol) was dissolved in 1 mL of hybridization buffer (10 mM Tris-HCl, 10 mM $MgCl_2$, pH 7.0) to measure fluorescence intensity. The fluorescence intensity obtained was defined as F0. Then there was added RNA sample (50 µL) to obtain RNA/DNA hybrid. Each hybrid was then treated with ribonuclease A (0.5 µg), followed by the measurement of fluorescence intensity, in which the fluorescence intensity obtained was defined as F1. Fluorescence quenching rate (Qr) was calculated by the formula 1 given below.

Figure 3:
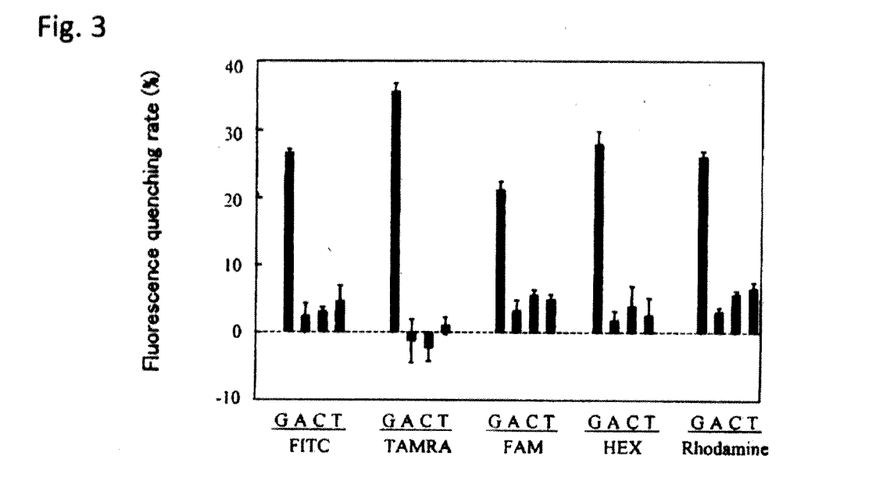
FIG. 3 demonstrates that the gene mutation of HBV can be detected through the fluorescence quenching rate in accordance with the present invention (Example 1).

The results are shown in FIG. 3. It was found that, when RNA sample was completely complementary to fluorescence-labeled probe (i.e. in the case of RNA derived from control (wild-type) gene sample/DNA hybrid, in which the base to be detected was G), a high fluorescence quenching rate was produced, whereas, when there was no complementation at the terminal site (i.e. in the case of RNA derived from target (mutant) gene sample/DNA hybrid, in which the base to be detected is other than G), a greatly decreased fluorescence quenching rate was produced. Thus, gene mutation can be detected through the fluorescence intensity measurement before and after the hybridization, followed by the calculation.

Figure 6:
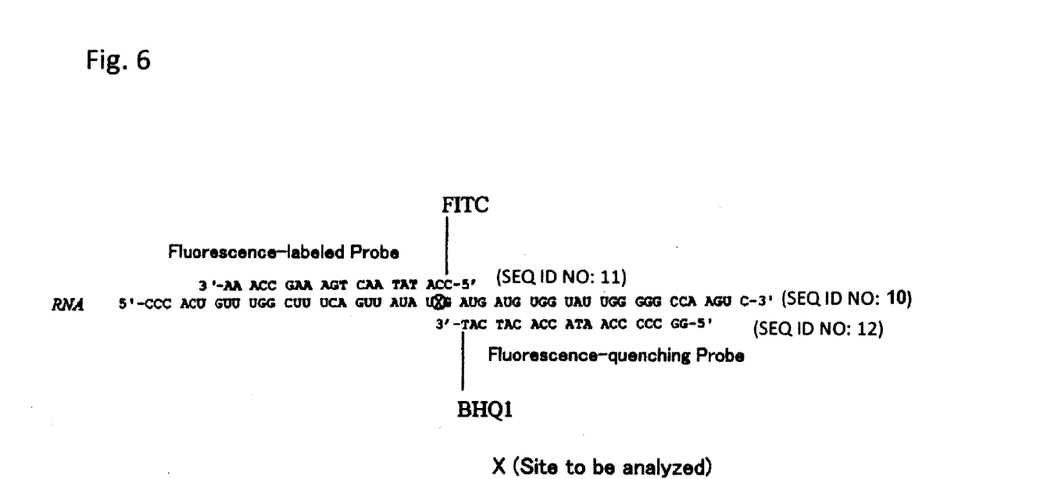
FIG. 6 shows a hybrid of HBV gene combined concurrently with a fluorescence-labeled probe and a fluorescence-quenching probe, as an example to which the present invention is applied (Example 1).

1.3.2 Mutation Detection by Simultaneous Use of Fluorescence-Labeled Probe and Fluorescence-Quenching Probe As shown in FIG. 6 there were used fluorescence-labeled probe composed of oligoDNA (5'-CCATATAACTGAAAGCCAAA-3') (SEQ ID NO: 11) with fluorescence dye (FITC) being combined with the 5'-end thereof and fluorescence-quenching probe composed of oligoDNA (5'-GGCCCCCAATACCACATCAT-3') (SEQ ID NO: 12) with fluorescence-quenching molecule (BHQ-1) being combined with the 3'-end thereof.

Fluorescence-labeled probe (20 pmol) and fluorescence-quenching probe (100 pmol) were dissolved in 1 mL of hybridization buffer (10 mM, Tris-HCl, 10 mM $MgCl_2$, pH 7.0) to measure fluorescence intensity. The fluorescence intensity obtained was defined as F0. Then there was added RNA sample (15 µL) to obtain RNA/DNA hybrid. The hybrid was then treated with ribonuclease A (0.5 µg), followed by the measurement of fluorescence intensity, in which the fluorescence intensity obtained was defined as F1. Fluorescence quenching rate (Qr) was calculated by the formula 1 given below.

Figure 7:
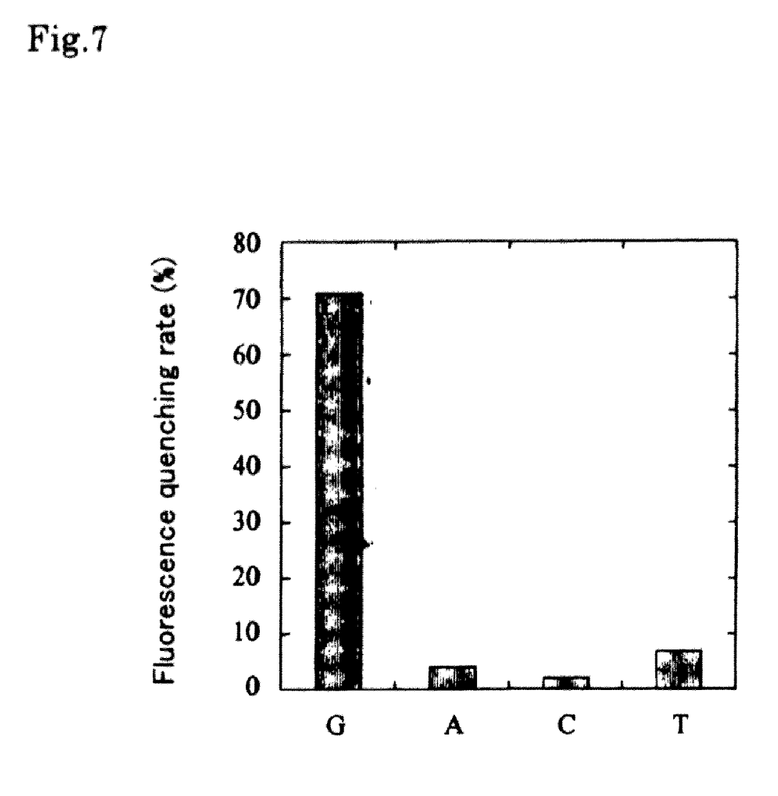
FIG. 7 demonstrates that, in the detection of HBV gene mutation in accordance with the present invention, the concurrent presence of a fluorescence-labeled probe and a fluorescence-quenching probe will lead to an enhanced quenching rate, thereby enabling highly sensitive detection of the mutation (Example 1).

The results are shown in FIG. 7. It was found that, when RNA sample was completely complementary to fluorescence-labeled probe (i.e. in the case of RNA derived from standard (wild-type) gene sample/DNA hybrid, in which the base to be detected was G), a high fluorescence quenching rate was produced, whereas, when there was no complementation at the terminal site (i.e. in the case of RNA derived from target (mutant) gene sample/DNA hybrid, in which the base to be detected was other than G), a greatly decreased fluorescence quenching rate was produced. Thus, gene mutation can be detected through the fluorescence intensity measurement before and after the hybridization, followed by the calculation.

Formula 1 $Qr=(F0-F1)/F0\times100(\%)$

EXAMPLE 2

Detection of Gene Mutation Observed in Aldehyde Hydrogenase Gene 1.1 Preparation of DNA (PCR)

PCR reactions were carried out using plasmid gene containing aldehyde hydrogenase gene (wild-type) (SEQ ID NO: 13) and plasmid gene containing aldehyde hydrogenase gene (mutant) (SEQ ID NO: 14) (FIG. 4) as template, to obtain gene fragments containing the sites to be detected, wherein each plasmid gene was composed of pUC18 with the SmaI site thereof being linked with aldehyde hydrogenase gene. As PCR primers there were used primer 1 having T7 RNA polymerase promoter sequence at the 5'-end thereof (SEQ ID NO:15) and primer 2 which was gene specific (SEQ ID NO:16) for DNA polymerase, Pyrobest® (TaKaRa). The reaction conditions were as follows:

Composition for PCR (100 µl): template DAN (<1 µg), DNA polymerase Pyrobest® (2.5 unit), primer 1 (1 µM), primer 2 (1 µM), dNTP (200 µm), 1×Pyrobest Buffer II.

PCR conditions: One cycle of thermal denaturation at 95° C., 15 sec, followed by thirty-five cycles of thermal denaturation at 95° C., 15 sec, annealing at 55° C., 30 sec, and then elongation reaction at 72° C., 30 sec.

Primer 1: 5'-ATGATCACTAATACGACTACACTATAGG-GTCAACTGCTATGATGTG-3' (SEQ ID NO: 15)

Primer 2: 5'-CCACACTCACAGTTTTCACTT-3' (SEQ ID NO: 16)

2.2 Preparation of RNA Samples (In Vitro Transcription)

The PCR products obtained by the step of 2.1 were subjected to in vitro transcription reactions to prepare single-stranded RNA. The transcription reactions were carried out using T7 RiboMAX™ Express Large Scale RNA Production System (Promega). The RNA products were recovered through ethanol precipitation, followed by redissolution in sterilized water to prepare RNA samples. The reaction conditions were as follows:

Composition for the reaction (20 µl): PCT product (1 µl), Enzyme Mix, T7 Express (2 µl), 1×RiboMAX™ Express T7 buffer.

Reaction conditions: Following the synthesis reaction (at 30° C., 30 min.), each RNA was recovered using Dr. GenTLM™ Precipitation Carrier (TaKaRa).

2.3. Hybridization and RNA Decomposition

Figure 4:
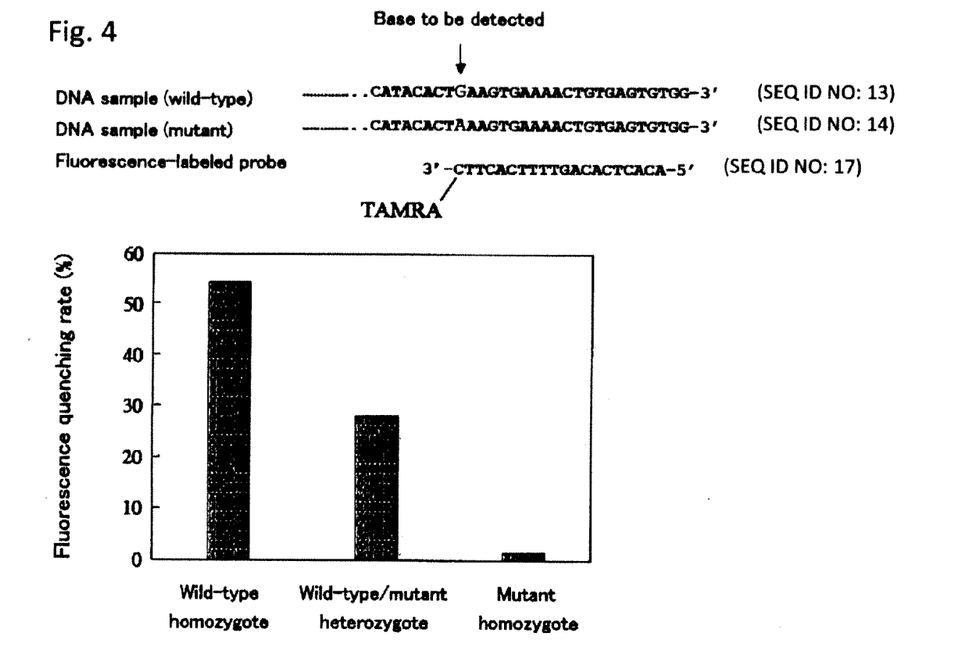
FIG. 4 shows the gene arrangements of aldehydehydrogenase and fluorescence-labeled probe for use in the detection of the mutation thereof (Example 2).
Figure 5:
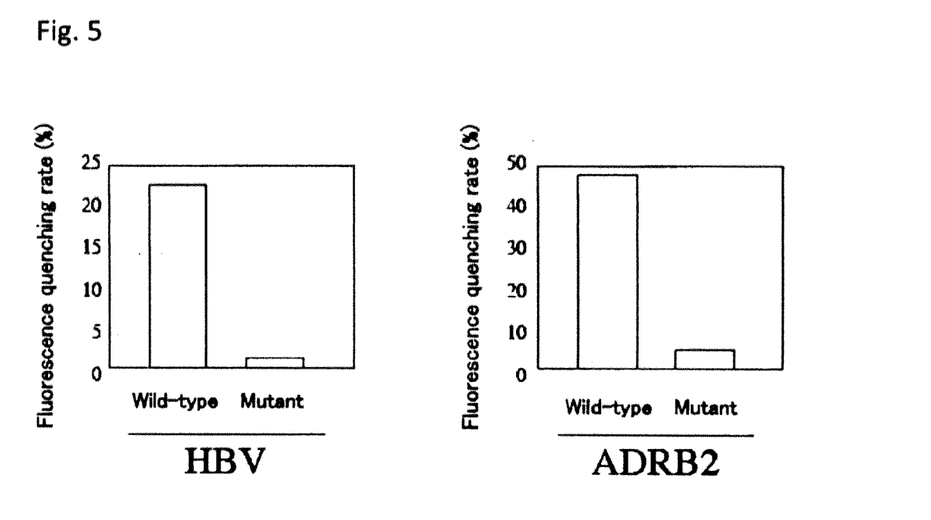
FIG. 5 demonstrates that the gene mutation of HBV and the gene mutation of ADRB2 can be simultaneously detected through the fluorescence quenching rate in accordance with the present invention (Example 3).

Fluorescence-labeled probe used was composed of oligoDNA (5'-ACACTCACAGTTTTCACTTC-3') (SEQ ID NO:17) being combined with fluorescence dye TAMRA at the 3'-end thereof, as shown in FIG. 4.

The fluorescence-labeled probe (40 pmole) was dissolved in 1 mL of hybridization buffer (10 mM Tris-HCl, 10 mM $MgCl_2$, pH 7.0) to measure fluorescence intensity. The fluorescence intensity obtained was defined as F0. Then there was added RNA sample (15 µL) to obtain RNA/DNA hybrid. Each hybrid was then treated with ribonuclease A (0.5 µg), followed by the measurement of fluorescence intensity, in which the fluorescence intensity obtained was defined as F1. Fluorescence quenching rate (Qr) was calculated by the above-mentioned formula.

The results are shown in FIG. 4. It was found that RNA sample derived only from the wild-type (wild-type homozygote) produced a high fluorescence quenching rate (55%). By contrast, RNA sample only from the mutant (mutant homozygote) produced a greatly decreased fluorescence quenching rate (2%). Heterozygote from the wild-type and the mutant produced a fluorescence quenching rate of 28%. Thus, allele mutation can be detected through the fluorescence intensity measurement before and after the hybridization, followed by the calculation.

EXAMPLE 3

Simultaneous Detection of Gene Mutations Observed in ADRB2 and Hepatitis B Virus 1.1 Preparation of DNA (PCR)

PCR reactions were carried out using plasmid genes containing human β2-Adrenergic Receptor (ADRB2) (wild-type and mutant) as template, to obtain gene fragments containing the sites to be detected. As PCR primers there were used primer 1 having T7 RNA polymerase promoter sequence at the 5'-end thereof (SEQ ID NO:18), and primer 2 which is gene specific (SEQ ID NO:19) with DNA polymerase, Pyrobest® (TaKaRa). The reaction conditions were as follows:

Composition for PCR (100 µl): template DNA (<1 µg), DNA polymerase Pyrobest® (2.5 unit), primer 1 (1 µM), primer 2 (1 µM), dNTP (200 µM), 1×Pyrobest Buffer II.

PCR Conditions: One cycle of thermal denaturation at 95° C., 15 sec, followed by thirty-five cycles of thermal denaturation at 95° C., 15 sec, annealing at 55° C., 30 sec, and then elongation reaction at 72° C., 30 sec.

SEQ ID NO: 18
Primer 1:    5'-ATGATCACTAATACGACTCACTATAGGGCTTTCCCCC

ACTGTTTGGC-3'

SEQ ID NO: 19
Primer 2:    5'-GGTACCCCAACTTCCAATTACATAT-3'

3.2 Preparation of RNA Samples (In Vitro Transcription)

The PCR products obtained by the step of 3.1 were subjected to in vitro transcription reactions to prepare single-stranded RNA. The transcription reactions were carried out using T7 RiboMAX™ Express Large Scale RNA Production System (Promega). The RNA products were recovered through ethanol precipitation, followed by redissolution in sterilized water to prepare RNA samples. The reaction conditions were as follows:

Composition for the reaction (20 µl): PCR product (each 2 µl), Enzyme Mix, T7 Express (2 µl), 1×RiboMAX™ Express T7 buffer.

Reaction conditions: Following the synthesis reaction (at 30° C., 30 min.), each RNA sample was recovered using Dr. GenTLM™ Precipitation Carrier (TaKaRa).

3.3 Hybridization and RNA Decomposition

There were used fluorescence-labeled probe composed of oligoDNA (5'-CCATATAACTGAAAGCCAAAC-3') (SEQ ID NO:20) with fluorescence dye FITC being combined to the 5'-end thereof, for HBV, and fluorescence-labeled probe composed of oligoDNA (5'-ACCCACACCTCGTC-CCTTTC-3') (SEQ ID NO:21) with fluorescence dye TAMRA being combined with the 3'-end thereof, for ADRB2.

Each fluorescence-labeled probe (40 pmol) was dissolved in 1 mL of hybridization buffer (10 mM Tris-HCl, 10 mM $MgCl_2$, pH 7.0) to measure fluorescence intensities from FITC and TAMRA. Each fluorescence intensity obtained was defined as F0. Then there was added RNA sample (15 µL) to obtain RNA/DNA hybrid. Each hybrid was then treated with ribonuclease A (0.5 µg), followed by the measurement of fluorescence intensity, in which the fluorescence intensity obtained was defined as F1. Fluorescence quenching rate (Qr) was calculated by the above-mentioned following formula. The results are shown in FIG. 3. The Qr values correspond to the respective degrees of complementarity in the hybrids, resulting in simultaneous detection of different types of plural SNPs. The results suggest that the present invention enables simultaneous detection of a plurality of SNPs present in different gene strands or in the same gene strand.

EXAMPLE 4

Identification of Tuna Varieties Through Gene Mutation 1.1 Preparation of DNA (PCR)

PCR reactions were carried out using mitochondrion (DNA of different varieties of tuna as template, to obtain gene fragments containing the sites to be detected. As PCR primers there were used primer 1 having T7 RNA polymerase promoter sequence at the 5'-end thereof (SEQ ID NO:22), and primer 2 which was gene specific (SEQ ID NO:23) with DNA polymerase, Pyrobest® (TaKaRa). The reaction conditions were as follows:

Composition for PCR (100 µl): template DNA (<1 µg), DNA polymerase Pyrobest® (2.5 unit), primer 1 (1 µm), primer 2 (1 µM), dNTP (200 µm), 1×Pyrobest Buffer II.

PCR conditions: One cycle of thermal denaturation at 95° C., 5 min, followed by thirty-five cycles of thermal denaturation at 95° C., 15 sec, annealing at 55° C., 30 sec, and then elongation reaction at 72° C., 30 sec.

SEQ ID NO: 22
Primer 1:    5'-ATGATCACTAATACGACTCACTATAGGGCTTTCCCCC

ACTGTTTGGC-3'

SEQ ID NO: 23
Primer 2:    5'-GGTACCCCAACTTCCAATTACATAT-3'

4.2 Preparation of RNA Samples (In Vitro Transcription)

The PCR products obtained by the step of 4.1 were subjected to in vitro transcription reactions to prepare single-stranded RNA. The transcription reactions were carried out using T7 RiboMAX™ Express Large Scale RNA Production System (Promega). The RNA probes were recovered through ethanol precipitation, followed by redissolution in sterilized water to prepare RNA samples. The reaction conditions were as follows:

Composition for the reaction (20 μL): PCR product (2 μl), Enzyme Mix, T7 Express (2 μL), 1×RiboMAX™ Express T7 buffer.

Reaction conditions: Following the synthesis reaction (at 30° C., 30 min.), each RNA sample was recovered using Dr. GenTLM™ Precipitation Carrier (TaKaRa).

Figure 8:
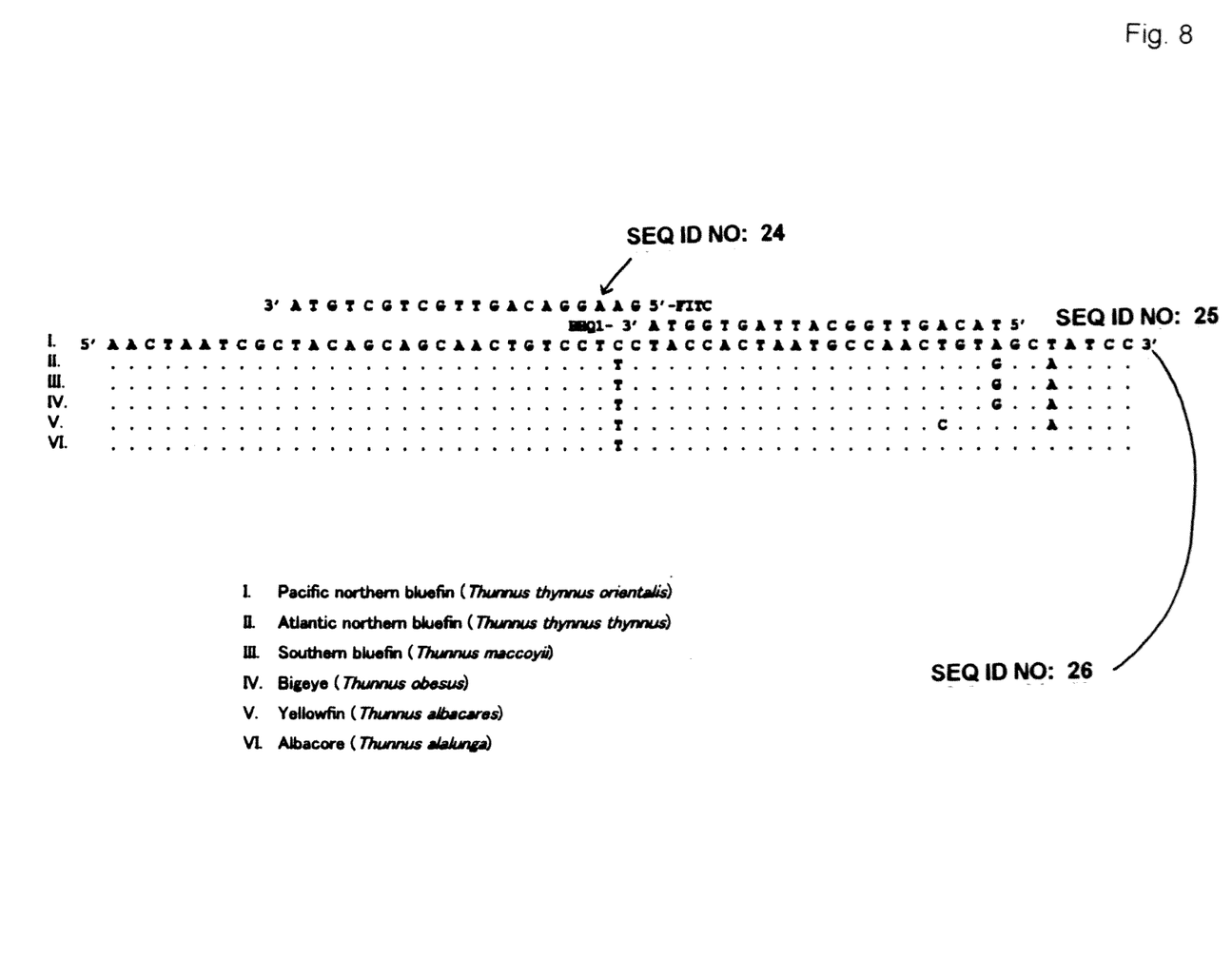
FIG. 8 shows the gene arrangements of different tunas in the identification of types or varieties of tuna in accordance with the present invention, and a fluorescence-labeled probe and a fluorescence-quenching probe used in the identification, in accordance with the present invention (Example 4).

4.3. Mutation Detection by Simultaneous Use of Fluorescence-Labeled Probe and Fluorescence-Quenching Probe As shown in FIG. 8 there were used fluorescence-labeled probe composed of oligo DNA (5'-GAAGGACAGTTGCTGCTGTA-3') (SEQ ID NO:24) with fluorescence dye (FITC) being combined with the 5'-end thereof and fluorescence-quenching probe composed of oligoDNA (5'-TACAGTTGGCATTAGTGGTA-3') (SEQ ID NO:25) with fluorescence-quenching molecule (BHQ-1) being combined with the 3'-end thereof.

The fluorescence-labeled probe (20 pmol) and the fluorescence quenching probe (100 pmol) were independently dissolved in 1 mL of hybridization buffer (10 mM Tris-HCl, 10 mM $MgCl_2$, pH 7.0) to measure fluorescence intensity. The fluorescence intensity obtained was defined as F0. Then there was added RNA sample (15 μL) to obtain RNA/DNA hybrid. Each hybrid was then treated with ribonuclease A (0.5 μg), followed by the measurement of fluorescence intensity, in which the fluorescence intensity obtained was defined as F1. Fluorescence quenching rate (Qr) was calculated by the above-mentioned formula 1. The aim of this example was to identify Pacific northern bluefin, the gene of which was thus the target gene. (SEQ ID NO:26)

Figure 9:
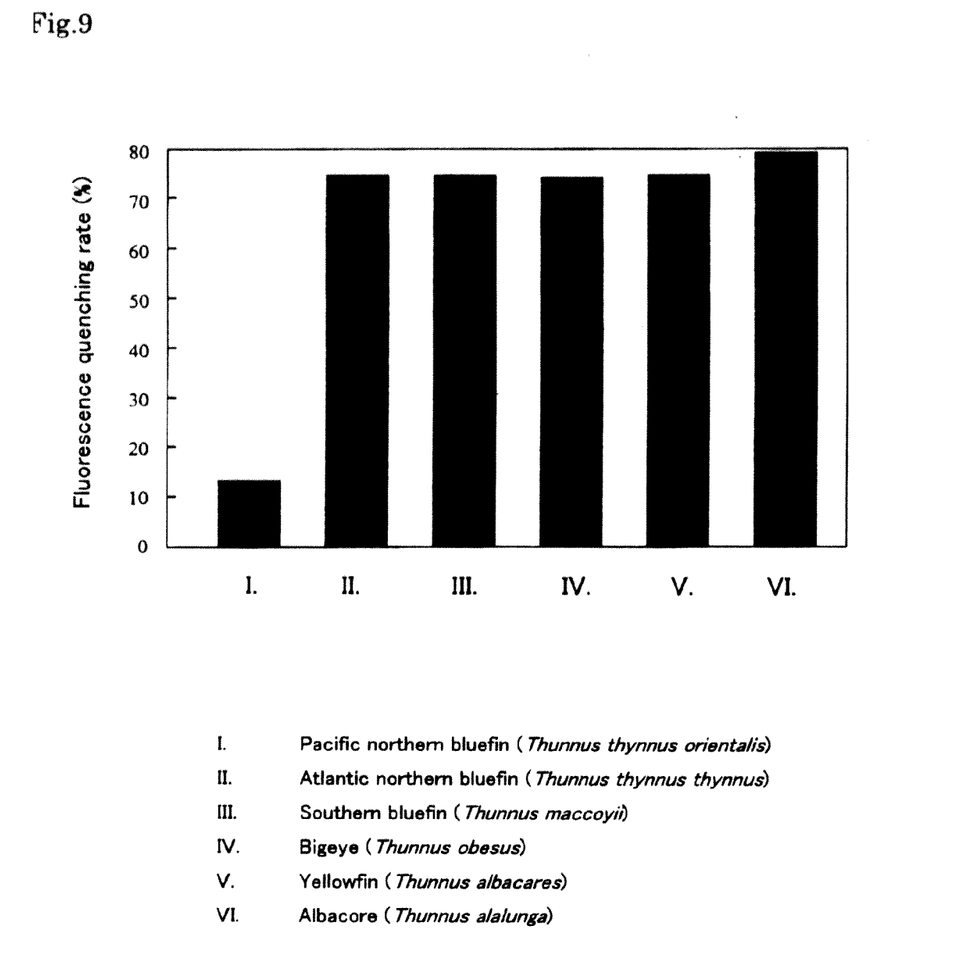
FIG. 9 shows the results of the identification of tuna varieties by measuring fluorescence quenching, in accordance with the present invention.

The results are shown in FIG. 9. It was found that, when RNA sample is completely complementary to the fluorescence-labeled probe (i.e. in the case of RNA derived from control gene sample/DNA hybrid, in which the base to be detected was T), a high fluorescence quenching rate was produced, whereas, when there is no complementation at the terminal site (i.e. in the case of RNA derived from target gene sample/DNA hybrid, in which the base to be detected was other than T), a greatly decreased fluorescence quenching rate is produced. Thus, Pacific northern bluefin can be identified through the fluorescence intensity measurement before and after the hybridization, followed by the calculation.

INDUSTRIAL UTILIZATION

The present invention enables the determination of mutation or presence/absence of a specific base in a gene in an easy and simple manner without any special equipment for analysis, and therefore is expected to be utilized in a variety of areas in industry including in the development of methods of diagnosis, prevention and therapy and medicine based on gene analysis, variety identification or breeding of agricultural, marine or livestock products, and the assessment of environmental variation.

What is claimed is:

1. A gene detecting method for determining mutation of a specific base or presence/absence of a specific base in a target gene, wherein there are provided a target gene sample and a control gene sample having a base sequence which is wild-type or standard-type with respect to the target gene, which method comprises steps of:
   (i) independently subjecting the target gene sample and the control gene sample to a polymerase chain reaction (PCR reaction) for amplification, using a primer in each reaction having an RNA polymerase promoter sequence at the 5'-end thereof,
   (ii) independently subjecting the double-stranded DNAs produced by said PCR reaction from the target gene sample and from the control gene sample, to an in vitro transcription reaction to form a single-stranded RNA,
   (iii) independently hybridizing the single-stranded RNAs with a fluorescence-labeled probe composed of a single-stranded DNA having a base sequence complementary to at least part of the base sequence of the control gene and being combined with a fluorescent dye, to form an RNA/DNA hybrid,
   (iv) subjecting the RNA/DNA hybrid obtained in step (iii) to RNA decomposition reaction using ribonuclease, and then
   (v) comparing the fluorescence intensity of the RNA/DNA hybrid derived from the target gene sample with that of the RNA/DNA hybrid derived from the control gene sample.

2. The method as claimed in claim 1, wherein in the step (iii) of forming RNA/DNA hybrids, each single-stranded RNA is hybridized with a fluorescence-quenching probe composed of a single-stranded DNA having a base sequence complementary to at least part of the base sequence of the control gene and being combined with a quenching dye which serves to quench the fluorescence dye.

* * * * *

SEQUENCE LISTING

```
<160> NUMBER OF SEQ ID NOS: 26

<210> SEQ ID NO 1
<211> LENGTH: 20
<212> TYPE: DNA
<213> ORGANISM: Homo sapiens

<400> SEQUENCE: 1
taatacgact cactataggg                                                   20

<210> SEQ ID NO 2
<211> LENGTH: 52
<212> TYPE: DNA
<213> ORGANISM: Hepatitis B virus

<400> SEQUENCE: 2
cccactgttt ggctttcagt tatatggatg atgtggtatt gggggccaag tc              52

<210> SEQ ID NO 3
<211> LENGTH: 52
<212> TYPE: DNA
<213> ORGANISM: Hepatitis B virus

<400> SEQUENCE: 3
cccactgttt ggctttcagt tatattgatg atgtggtatt gggggccaag tc              52
```

-continued

```
<210> SEQ ID NO 4
<211> LENGTH: 20
<212> TYPE: DNA
<213> ORGANISM: Artificial Sequence
<220> FEATURE:
<223> OTHER INFORMATION: fluorescent labeled probe

<400> SEQUENCE: 4
catataactg aaagccaaac                                                   20

<210> SEQ ID NO 5
<211> LENGTH: 16
<212> TYPE: PRT
<213> ORGANISM: Artificial Sequence
<220> FEATURE:
<223> OTHER INFORMATION: pUC18

<400> SEQUENCE: 5

His Cys Gly Ala Phe Ser Tyr Met Asp Asp Val Val Leu Gly Ala Lys
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: pUC18

<400> SEQUENCE: 6

His Cys Gly Ala Phe Ser Tyr Ile Asp Asp Val Val Leu Gly Ala Lys
1               5                   10                  15

<210> SEQ ID NO 7
<211> LENGTH: 47
<212> TYPE: DNA
<213> ORGANISM: Artificial Sequence
<220> FEATURE:
<223> OTHER INFORMATION: PRC Primer

<400> SEQUENCE: 7
atgatcacta atacgactca ctatagggct ttcccccact gtttggc                     47

<210> SEQ ID NO 8
<211> LENGTH: 25
<212> TYPE: DNA
<213> ORGANISM: Artificial Sequence
<220> FEATURE:
<223> OTHER INFORMATION: PRC Primer

<400> SEQUENCE: 8
ggtaccccaa cttccaatta catat                                             25

<210> SEQ ID NO 9
<211> LENGTH: 52
<212> TYPE: DNA
<213> ORGANISM: Artificial Sequence
<220> FEATURE:
<223> OTHER INFORMATION: PCR product of wild type HBV gene

<400> SEQUENCE: 9
cccactguuu ggcuuucagu uauauggaug augugguauu gggggccuug uc               52

<210> SEQ ID NO 10
<211> LENGTH: 52
<212> TYPE: DNA
<213> ORGANISM: Artificial Sequence
```

```
<220> FEATURE:
<223> OTHER INFORMATION: PCR product of mutant HBV gene

<400> SEQUENCE: 10
cccacuguuu ggcuuucagu uauauugaug auguggauau gggggccaag uc            52

<210> SEQ ID NO 11
<211> LENGTH: 20
<212> TYPE: DNA
<213> ORGANISM: Artificial Sequence
<220> FEATURE:
<223> OTHER INFORMATION: oligoDNA probe

<400> SEQUENCE: 11
catataactg aaagccaaac                                                20

<210> SEQ ID NO 12
<211> LENGTH: 20
<212> TYPE: DNA
<213> ORGANISM: Artificial Sequence
<220> FEATURE:
<223> OTHER INFORMATION: oligoDNA Probe

<400> SEQUENCE: 12
ggcccccaat accacatcat                                                20

<210> SEQ ID NO 13
<211> LENGTH: 30
<212> TYPE: DNA
<213> ORGANISM: Artificial Sequence
<220> FEATURE:
<223> OTHER INFORMATION: plasmid gene containing aldehyde hydrogenase
      gene (wild type)

<400> SEQUENCE: 13
catacactga agtgaaaact gtgagtgtgg                                     30

<210> SEQ ID NO 14
<211> LENGTH: 30
<212> TYPE: DNA
<213> ORGANISM: Artificial Sequence
<220> FEATURE:
<223> OTHER INFORMATION: plasmid gene containing aldehyde hydrogenase
      gene (mutant)

<400> SEQUENCE: 14
catacactaa agtgaaaact gtgagtgtgg                                     30

<210> SEQ ID NO 15
<211> LENGTH: 45
<212> TYPE: DNA
<213> ORGANISM: Artificial Sequence
<220> FEATURE:
<223> OTHER INFORMATION: PCR Primer

<400> SEQUENCE: 15
atgatcacta atacgactca ctatagggtc aactgctatg atgtg                    45

<210> SEQ ID NO 16
<211> LENGTH: 21
<212> TYPE: DNA
<213> ORGANISM: Artificial Sequence
<220> FEATURE:
<223> OTHER INFORMATION: PCR Primer
```

```
<400> SEQUENCE: 16
ccacactcac agttttcact t                                              21

<210> SEQ ID NO 17
<211> LENGTH: 20
<212> TYPE: DNA
<213> ORGANISM: Artificial Sequence
<220> FEATURE:
<223> OTHER INFORMATION: oligoDNA probe

<400> SEQUENCE: 17
acactcacag ttttcacttc                                                20

<210> SEQ ID NO 18
<211> LENGTH: 47
<212> TYPE: DNA
<213> ORGANISM: Artificial Sequence
<220> FEATURE:
<223> OTHER INFORMATION: PCR Primer

<400> SEQUENCE: 18
atgatcacta atacgactca ctatagggct ttcccccact gtttggc                  47

<210> SEQ ID NO 19
<211> LENGTH: 25
<212> TYPE: DNA
<213> ORGANISM: Artificial Sequence
<220> FEATURE:
<223> OTHER INFORMATION: PCR Primer

<400> SEQUENCE: 19
ggtaccccaa cttccaatta catat                                          25

<210> SEQ ID NO 20
<211> LENGTH: 21
<212> TYPE: DNA
<213> ORGANISM: Artificial Sequence
<220> FEATURE:
<223> OTHER INFORMATION: oligoDNA Probe

<400> SEQUENCE: 20
ccatataact gaaagccaaa c                                              21

<210> SEQ ID NO 21
<211> LENGTH: 20
<212> TYPE: DNA
<213> ORGANISM: Artificial Sequence
<220> FEATURE:
<223> OTHER INFORMATION: oligoDNA probe

<400> SEQUENCE: 21
acccacacct cgtcccttc                                                 20

<210> SEQ ID NO 22
<211> LENGTH: 47
<212> TYPE: DNA
<213> ORGANISM: Artificial Sequence
<220> FEATURE:
<223> OTHER INFORMATION: PCR Primer

<400> SEQUENCE: 22
atgatcacta atacgactca ctatagggct ttcccccact gtttggc                  47
```

-continued

```
<210> SEQ ID NO 23
<211> LENGTH: 25
<212> TYPE: DNA
<213> ORGANISM: Artificial Sequence
<220> FEATURE:
<223> OTHER INFORMATION: PCR Primer

<400> SEQUENCE: 23
ggtaccccaa cttccaatta catat                                          25

<210> SEQ ID NO 24
<211> LENGTH: 20
<212> TYPE: DNA
<213> ORGANISM: Artificial Sequence
<220> FEATURE:
<223> OTHER INFORMATION: oligoDNA probe

<400> SEQUENCE: 24
gaaggacagt tgctgctgta                                                20

<210> SEQ ID NO 25
<211> LENGTH: 20
<212> TYPE: DNA
<213> ORGANISM: Artificial Sequence
<220> FEATURE:
<223> OTHER INFORMATION: oligoDNA probe

<400> SEQUENCE: 25
tacagttggc attagtggta                                                20

<210> SEQ ID NO 26
<211> LENGTH: 57
<212> TYPE: DNA
<213> ORGANISM: Thunnus thynnus

<400> SEQUENCE: 26
aactaatcgc tacagcagca actgtcctcc taccactaat gccaactgta gctatcc       57
```